United States Patent [19]

Handy

[11] Patent Number: 4,773,259
[45] Date of Patent: Sep. 27, 1988

[54] MODIFIED BOREHOLE SHEAR TESTER

[75] Inventor: Richard L. Handy, Ames, Iowa

[73] Assignee: Iowa State University Research Foundation, Inc., Ames, Iowa

[21] Appl. No.: 60,824

[22] Filed: Jun. 12, 1987

[51] Int. Cl.$^4$ .............................................. G01N 3/00
[52] U.S. Cl. ............................................ 73/84; 73/784
[58] Field of Search ................ 73/784, 84, 151, 865.6, 73/841

[56] References Cited

U.S. PATENT DOCUMENTS

| | | | |
|---|---|---|---|
| 3,175,392 | 3/1965 | Tharalson et al. | 73/84 |
| 3,427,871 | 2/1969 | Handy et al. | 73/84 |
| 3,499,320 | 3/1970 | Fox et al. | 73/784 |
| 3,673,861 | 7/1972 | Handy | 73/841 |
| 3,772,911 | 11/1973 | Ruppeneit et al. | 73/784 |
| 3,872,717 | 3/1975 | Fox | 73/84 |
| 4,400,970 | 8/1983 | Ali | 73/84 |
| 4,539,851 | 9/1985 | Lutenegger | 73/784 |
| 4,557,147 | 12/1985 | Rohde et al. | 73/784 |

FOREIGN PATENT DOCUMENTS 0092211  6/1982  Japan ...................... 73/84

OTHER PUBLICATIONS

"The Modified Borehole Shear Device", J. P. Demartinecourt and Gunther E. Bauer.
"Borehole Shear Test and Slope Stability", Richard L. Handy.

Primary Examiner—Stewart J. Levy
Assistant Examiner—Robert R. Raevis
Attorney, Agent, or Firm—Zarley, McKee, Thomte, Voorhees & Sease

[57] ABSTRACT

A conventional borehole shear tester is modified by incorporating a volume-monitoring accessory in the non-pressurized chamber vent line. This accessory includes a fluid reservoir operatively connected to the non-pressurized chamber of the shear head unit. A change in the level of fluid in the reservoir indicates changes in the volume of the non-pressurized chamber, which in turn indicates a change in shear head diameter. By maintaining a constant fluid level in the reservoir, the volume of the non-pressurized chamber remains constant and the shear head diameter remains constant. Thus, with the shear head diameter fixed, the normal pressure exerted on the wall of the borehole varies as the soil dilates or consolidates. Accordingly, the modified borehole shear tester of the present invention simulates friction pile behavior.

12 Claims, 1 Drawing Sheet

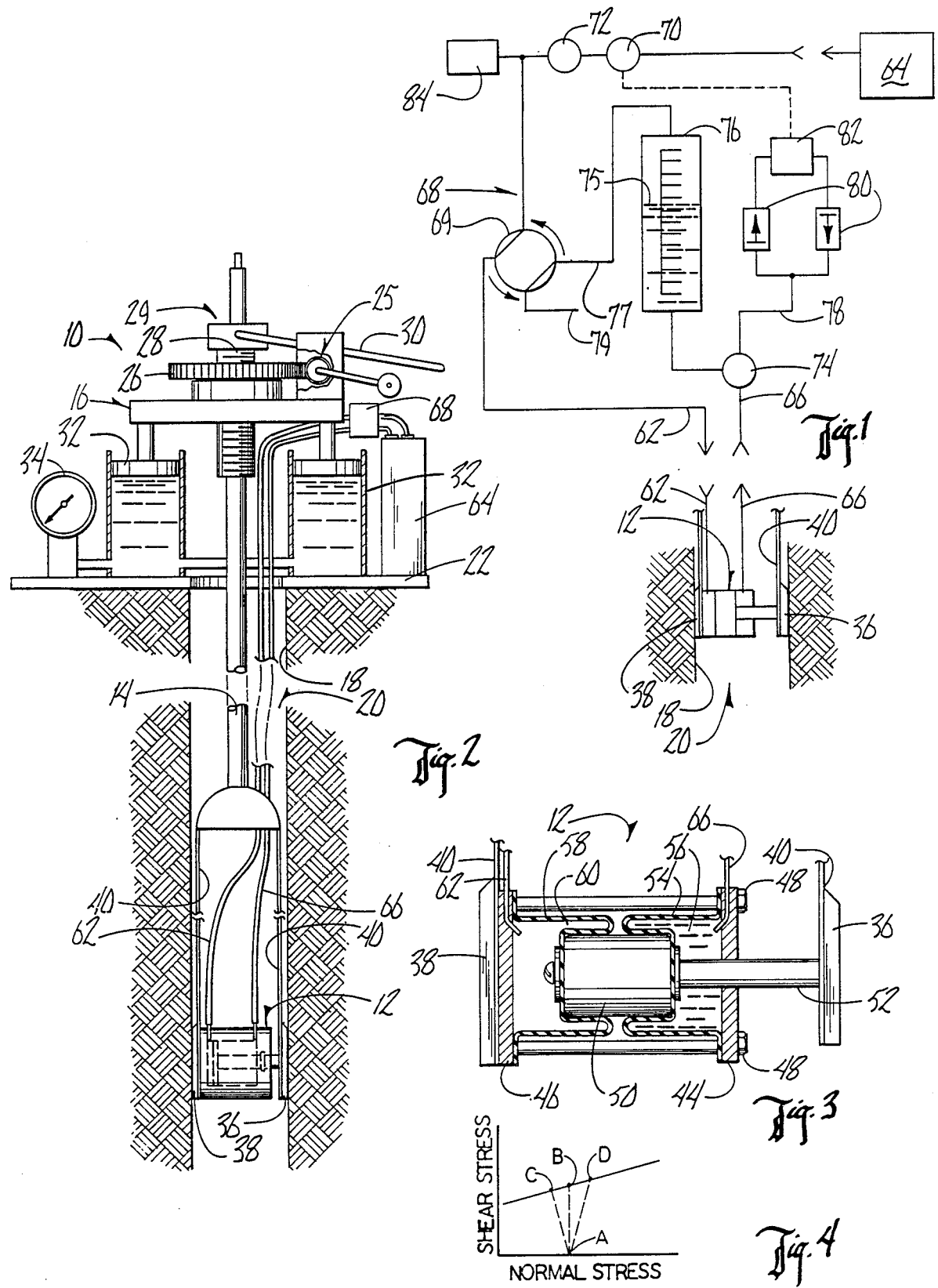

MODIFIED BOREHOLE SHEAR TESTER

BACKGROUND OF THE INVENTION

A conventional borehole shear testing device measures soil shearing strength by means of two diametrically opposed shear plates. The shear plates apply a normal stress to the soil forming the wall of the borehole. An axial force is exerted on the shear plates such that the soil shears axially along the borehole. During this conventional test, the normal stress is held constant while the shear head diameter, that is, the distance between the opposing shear plates, is allowed to vary in response to consolidation or dilation of the soil. If the soil consolidates, the head diameter increases. If the soil dilates, the head diameter decreases.

The conventional borehole shear tester imperfectly models the behavior of pile under load. This problem exists because the pile has a constant diameter, and therefore the pile will not yield or compress as the soil consolidates or dilates. Accordingly, in order to simulate pile behavior, the head diameter must be held constant, contrary to the conventional use of the borehole shear tester.

A primary objective of the present invention is the provision of a modified borehole shear tester which simulates pile behavior and which produces a soil normal stress similar to that which develops against a pile surface upon axial loading.

Another objective of the present invention is the provision of an accessory device that can be quickly and easily connected to a conventional borehole shear tester for simulating pile behavior.

A further objective of the present invention is the provision of a method and means for determining soil dilation and consolidation.

Still another objective of the present invention is the provision of a means and method for maintaining a constant shear head diameter while the soil is sheared.

Another objective of the present invention is the provision of a method and means for measuring the normal force and the shearing force as the soil shears, thereby simulating the skin friction on a pile at the moment of failure.

SUMMMARY OF THE INVENTION

The present invention utilizes an accessory to a conventional borehole shear tester such that in situ determinations of soil consolidation and dilation can be determined. As such, the modified borehole shear tester of the present invention simulates friction pile behavior and resolves the soil normal stress against the pile surface.

The conventional borehole shear tester includes a shear head unit with expandable shear plates operatively connected to a pressure cylinder unit having opposite pressurized and non-pressurized chambers. The shear heads are conventionally expanded by gas so as to exert a normal force on the soil while an axial force is exerted on the shear head unit so as to cause the soil to shear. In the modified device, a fluid reservoir is operatively connected to the non-pressurized chamber and the level of liquid in the reservoir is maintained constant by adjusting the quantity of gas in the pressurized chamber. The amount of liquid in the reservoir is dependent upon the volume of the non-pressurized chamber, which in turn is inversely related to the shear head diameter. Thus, the shear head diameter is maintained constant, thereby simulating pile. As the soil shears, both normal stress and shear stress are measured. Since the shear head diameter is held constant, an increase in the normal stress indicates soil dilation while a decrease in normal stress indicates soil consolidation.

BRIEF DESCRIPTION OF THE DRAWINGS

FIG. 1 is a schematic view of the modified borehole shear tester of the present invention.

FIG. 2 is a sectional side elevation view of the borehole shear tester.

FIG. 3 is a sectional side elevational view of the shear head unit of the borehole shear tester.

FIG. 4 is a graph depicting soil consolidation and dilation.

DETAILED DESCRIPTION OF THE DRAWINGS

A conventional borehole shear tester is generally designated by the reference numeral 10, and is substantially shown in FIG. 2 of the drawings. Tester 10 includes a shear head unit 12 mounted on a pull rod 14, means 16 for exerting an axial force on shear head unit 12, and means for exerting a normal force on the soil forming the wall 18 of the borehole 20.

Axial force means 16 includes a base plate 22 through which pull rod 14 extends, and which engages the ground surface. A crank and worm gear 25 drives a gear 26 turning on a threaded hollow shaft 28 held by a clamp 29 to pull rod 14 so as to exert a pulling force on pull rod 14. A torque arm 30 prevents the rod and shear head from turning. A pair of hydraulic reaction cylinders 32 are coupled with a hydraulic pressure gauge or transducer 34 so that the pulling force and thus the shear stress can be measured.

The shear head unit 12 is shown in further detail in FIG. 3. This structure is described in detail in applicant's previous U.S. Pat. No. 3,673,861. Generally, shear head unit 12 includes opposite shear plates 36, 38 which are connected to straps 40, which in turn are connected to pull rod 14. Plates 36 and 38 normally have a plurality of soil-engaging teeth thereon, but are shown to be smooth in the drawings so as to simulate the smooth pile surface, such as a concrete or steel piling. The ends of the shear plates are beveled or sharpened to reduce their end effect as they are pulled upward, which would tend to obscure the desired measurement.

A pair of cylinder end plates 44, 46 are secured to each other by bolts 48. A piston 50 is secured to shear plate 36 by a piston rod 52 which extends through an aperture in end plate 44. A first flexible bellows member 54 is secured to end plate 44 and one end of piston 50 so as to form a first chamber 56 while a second flexible bellows member 58 is secured to end plate 46 and the opposite end of piston 50 so as to form a second chamber 60. A flexible gas inlet line 62 provides communication between a gas source 64 and second chamber 60, such that chamber 60 is pressurized. A vent line 66 normally provides communication between chamber 56 and the atmosphere such that chambers 56 is non-pressurized. Thus, when gas is introduced through inlet line 62 into pressurized chamber 60, shear plate 36 expands in a direction away from shear plate 38 such that plates 36, 38 engage the wall 18 of bore hole 20 and exert a normal stress thereon. Upon completion of the shear test, vent line 66 can be operatively connected to gas source 64 and inlet line 62 vented to the atmosphere so that shear plate 36 can be retracted in a direction toward shear plate 38 such that shear head unit 12 can be removed from the bore hole.

The above description sets forth the basic structure and operation of the conventional borehole shear tester. The following description sets forth the accessory device to the borehole shear tester which allows soil consolidation and dilation to be ascertained while simulating pile behavior.

The accessory device is generally designated by the reference numeral 68 and is connected to inlet line 62 and vent line 66. Device 68 includes a gas source 64 connected to a self-bleeding regulator 70, and a normal pressure gauge 72 connected through a selector valve 69 to an inlet line 62 between gas source 64 and pressurized chamber 60. A graduated reservoir 76 is connected in vent line 66 connecting to non-pressurized chamber 56. This unpressurized system, including chamber 56, is filled with liquid to an arbitrary level 75 and vented to atmospheric pressure through line 77 connecting to valve 69 and outlet 79. An optional selector valve 74 and auxiliary line 78 provides communication between line 66 and sensitive pressure switches 80 to provide an impulse to drive a servo-motor 82 optionally attached to regulator 70. Also, an optional transducer 84 can be connected to normal pressure gauge 72 to convey the gauge reading to a readout device.

In operation, the modified borehole shear tester having accessory device 68 is positioned in borehole 20 and shear plates 36, 38 are expanded in the conventional fashion. Once the initial normal force exerted by shear plates 36, 38 on wall 18 of borehole is achieved, the liquid level 75 in reservoir 76 is observed. To simulate friction pile behavior, it is desirable to maintain shear plates 36, 38 in a fixed expanded position, since the diameter of a pile is constant. The diameter of the shear plates 36, 38, that is, the spacing therebetween, is inversely related to the volume of non-pressurized chamber 56. Any change in the volume of non-pressurized chamber 56 will cause a change in the level of liquid in reservoir 76. Thus, by maintaining a constant liquid level in reservoir 76, the volume of non-pressurized chamber 56 will remain constant and the shear head diameter will remain constant. Thus, friction pile behavior can be simulated.

As the soil of borehole wall 18 begins to fail or shear in response to the axial shearing stress exerted by pull rod 14, the soil may dilate or consolidate. During dilation, the soil voids expand as particles move with respect to one another, a result being to exert a greater force on shear plates 36, 38. Such increased soil pressure tends to reduce the shear head diameter. However, any movement of plate 36 towards plate 38 will enlarge the volume of non-pressurized chamber 56, which will be indicated by a drop in the liquid level in reservoir 76. However, to counteract the increased soil pressure as indicated by the level of liquid in reservoir 76, regulator 70 can be actuated manually or by servo-motor 82 to provide additional gas to pressurized chamber 60 so as to maintain a constant shear head diameter, as indicated by the level of liquid in reservoir 76.

Conversely, during soil consolidation, the soil particles compact with respect to one another, so as to produce reduced soil pressure on shear plates 36, 38. Such a reduced soil pressure tends to allow shear plate 36 to expand with respect to shear plate 38, and thus reduce the volume of non-pressurized chamber 56, as registered by the level of liquid in reservoir 76. When such a change in the liquid level commences, regulator 70 can be manually or automatically self-bled to relieve pressure from pressurized chamber 60 to thereby maintain a constant shear head diameter. An automatic method for providing these pressure adjustments is by means of the optional valve 74, whereby the liquid instead of being conveyed to a graduated reservoir that is vented to the atmosphere, remains in a closed system and actuates one or the other of the pressure switches 80 when a change in liquid volume and base liquid pressure occurs and thereby causing servo-motor 82 to adjust regulator 70 so as to maintain a constant shear head diameter.

Upon completion of a test, valve 69 is turned so as to reverse the pressurized and unpressurized lines 62 and 66 so gas pressure now enters to the liquid surface 75 in reservoir 76, forcing liquid down line 66 to close the shear head 20 for withdrawal from the hole. Simultaneously valve 69 opens the normally pressurized line 62 to the atmosphere 79.

The classical Coulomb relationship between shear stress and normal stress can be developed by plotting the data from several shear tests conducted along the borehole. On the graph depicted in FIG. 4, point A represents the normal stress initially applied during a shear test. Point B corresponds to the stresses of non-consolidating and non-dilating soil, whereas points C and D represent stresses of consolidating soil and dilating soil, respectively. The difference in normal stress between point D and point C or point B, represents the change in soil pressure on pile during consolidation or dilation of the soil, respectively.

Points C and D are not ascertainable using the conventional methods of the borehole shear tester, since the normal stress is held constant in such conventional tests. In these conventional tests, the shear head diameter is allowed to vary depending on the soil consolidation or dilation. In comparison, in using the modified borehole shear tester of the present invention, shear head diameter is maintained at a constant, while normal stress is allowed to vary in response to soil consolidation or dilation. Thus, with the present methodology, both the normal stress and the shear stress are measured continuously during shearing of the soil.

Also, it is preferable to monitor the volume of non-pressurized chamber 56, rather than pressurized chamber 60, since pressurized inlet line 62 is made of nylon and therefore tends to stretch as pressure increases. Thus, any regulation of volume of non-pressurized chamber 56 will have an associated error.

It is understood that other means may be employed for monitoring the shear head diameter without departing from the scope of the present invention. For example, the diameter can be electrically monitored by a linear variable differential transformer (LVDT).

From the foregoing, it can be seen that the present invention accomplishes at least all of the stated objectives.

What is claimed is:

1. A method of in-situ determination of soil dilation and consolidation, comprising:
   forming a borehole in the soil;
   introducing a borehole shear tester into the borehole, said tester including a shear head unit with expandable shear plates operatively connected to a pressure cylinder unit with opposite pressurized and non-pressurized volume-variable chambers;

expanding said shear plates into engagement with the soil surrounding the borehole so as to exert an initial normal force on the soil;

measuring the initial normal force;

moving said shear head unit axially along said borehole to induce a shearing force on the soil while holding the distance between the shear plates constant as the soil shears; and measuring the normal force as the soil shears whereby an increasing normal force indicates soil dilation and a decreasing normal force indicates soil consolidation.

2. The method of claim 1 wherein said normal force varies as soil dilation or consolidation occurs.

3. The method of claim 1 wherein a gas is introduced through a self-bleeding regulator into said pressurized chamber to expand said shear plates, said method further including regulating the quantity of gas in said pressurized chamber such that the volume of said non-pressurized chamber remains constant.

4. The method of claim 3 wherein additional gas is introduced into said pressurized chamber when the soil is dilating and gas is bled from said pressurized chamber when the soil is consolidating.

5. The method of claim 1 wherein the volume of said non-pressurized chamber is maintained constant by monitoring a liquid level in a liquid reservoir operatively connected to said non-pressurized chamber.

6. The method of claim 1 further including measuring soil shear stress and the normal force as the soil shears.

7. An improved borehole shear testing device for in situ determination of soil dilation and consolidation, said device being adapted for insertion into a borehole and including a shear head unit with expandable shear plates operatively connected to a pressure cylinder unit with opposite pressurized and non-pressurized volume-variable chambers, means for expanding said shear plates so as to exert a normal stress on the soil forming the wall of the borehole, and means for exerting an axial force on said shear head unit, said improvement comprising:

means for maintaining said shear plates in a fixed position relative to one another during the shear testing of the soil, whereby dilation or consolidation of the soil is ascertained by changes in the normal stress.

8. The improved device of claim 7 wherein the volume of said non-pressurized chamber is inversely related to the expansion of said shear plates, and said means for maintaining said shear plates in a fixed position includes a fluid reservoir operatively connected to said non-pressurized chamber, the level of fluid in the reservoir being maintained constant by adjusting the quantity of gas in said pressurized chamber as the soil dilates or consolidates such that the volume of the non-pressurized chamber and thus the relative position of the shear plates is maintained constant.

9. The improved device of claim 8 wherein a servo-motor automatically adjusts the quantity of gas in said pressurized chamber in response to pressure changes in said non-pressurized chamber.

10. The improved device of claim 9 wherein pressure switch means sense pressure changes in said non-pressurized chamber so as to activate said servo-motor.

11. The improved device of claim 7 wherein the volume of the chambers are related to the expansion of the shear plates, and said means for maintaining said shear plates in a fixed position includes a fluid reservoir operatively connected to one of said chambers, the level of fluid in the reservoir being maintained constant by adjusting the quantity of gas in said pressurized chamber as the soil dilates or consolidates such that the volume of said one chamber and thus the relative position of the shear plates is maintained constant.

12. The improved device of claim 11 wherein said one chamber is the non-pressurized chamber.

* * * * *